US00PP32918P2

(12) United States Plant Patent
Holtmaat

(10) Patent No.: US PP32,918 P2
(45) Date of Patent: Mar. 23, 2021

(54) ***RUDBECKIA* PLANT NAMED 'RUDLE169'**

(50) Latin Name: *Rudbeckia hirta*
Varietal Denomination: RUDLE169

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,133

(22) Filed: Feb. 7, 2020

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474, 428
CPC ..... A01H 5/02; A01H 5/00; A01H 6/14
See application file for complete search history.

(56) References Cited

PUBLICATIONS

AB Cultivars *Rudbeckia* 'Lemon', retrieved on Jul. 30, 2020, retrieved from the Internet at https://www.ab-cultivars.com/?portfolio=rudbeckia-lemon-smileyz, one page. (Year: 2020).*
Vitroflora by Beppler Kft Perennials & Grasses 2020, retrieved on Jul. 28, 2020, retrieved from the Internet at https://issuu.com/bepplerkft/docs/vitroflora_evelo_katalogus_2020, cover page, pp. 2-3, 92-94, 126, 144. (Year: 2019).*

* cited by examiner

*Primary Examiner* — June Hwu
(74) *Attorney, Agent, or Firm* — Penny J. Aguirre

(57) ABSTRACT

A new cultivar of *Rudbeckia* plant named 'RUDLE169' that is characterized by its short plant height, its well-branched plant habit, its strong stems, its very floriferous blooming habit, its long flowering period, and its inflorescences with ray florets that are deep yellow-orange in color with yellow tips and disk florets that are green-yellow in color.

2 Drawing Sheets

Botanical classification: *Rudbeckia hirta.*
Variety denomination: 'RUDLE169'.

CROSS-REFERENCE TO A RELATED APPLICATION

This application is related to a European plant breeders' rights application filed on Sep. 3, 2018, application No. 2018/2259. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Rudbeckia hirta* and will hereafter by referred to by its cultivar name 'RUDLE169'. The new cultivar is an herbaceous perennial grown for use as a landscape plant.

'RUDLE169' was derived from a breeding program in July of 2016 conducted by the Inventor at a nursery in Zuidwolde, The Netherlands. The objective of the breeding program was to select new cultivars of *Rudbeckia* with floriferous blooming habits and compact plant habits.

'RUDLE169' was selected in July of 2017 by the Inventor from amongst seedlings in a trial field that had been planted with seed derived from open pollination of numerous unpatented and unnamed proprietary plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in January of 2018. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDLE169' as a unique cultivar of *Rudbeckia.*

1. 'RUDLE169' exhibits a short plant height.
2. 'RUDLE169' exhibits a well-branched plant habit.

3. 'RUDLE169' exhibits strong stems.
4. 'RUDLE169' exhibits a very floriferous blooming habit.
5. 'RUDLE169' exhibits a long flowering period.
6. 'RUDBR169' exhibits inflorescences with ray florets that are deep yellow-orange in color with yellow tips and disk florets that are green-yellow in color.

'RUDLE169' can be compared to the *Rudbeckia* cultivars SMILEYZ® 'Chocolate' (not patented), and SMILEYZ® 'Sunny' (not patented). SMILEYZ® 'Chocolate' is similar to 'RUDLE169' in plant height and in having strong stems. SMILEYZ® 'Chocolate' differs from 'RUDLE169' in commencing bloom earlier in the season season, ray florets that are dark grey-orange to brown in color, and inflorescence discs that are brown in color. SMILEYZ® 'Sunny' is similar to 'RUDLE169' in having strong stems. SMILEYZ® 'Sunny' differs from 'RUDLE169' in having a considerably larger plant height, ray florets that are lighter yellow-orange in color and inflorescence discs that are brown in color.

BRIEF DESCRIPTION OF THE DRAWINGS

The accompanying colored photographs illustrate the overall appearance and distinct characteristics of the new *Rudbeckia*. The photographs were taken of a 4-month-old plant of 'RUDLE169' as grown outdoors in a 17-cm container in Zuidwolde, The Netherlands.

The photograph in FIG. 1 is a side view of 'RUDLE169' in bloom.

Figure 1:
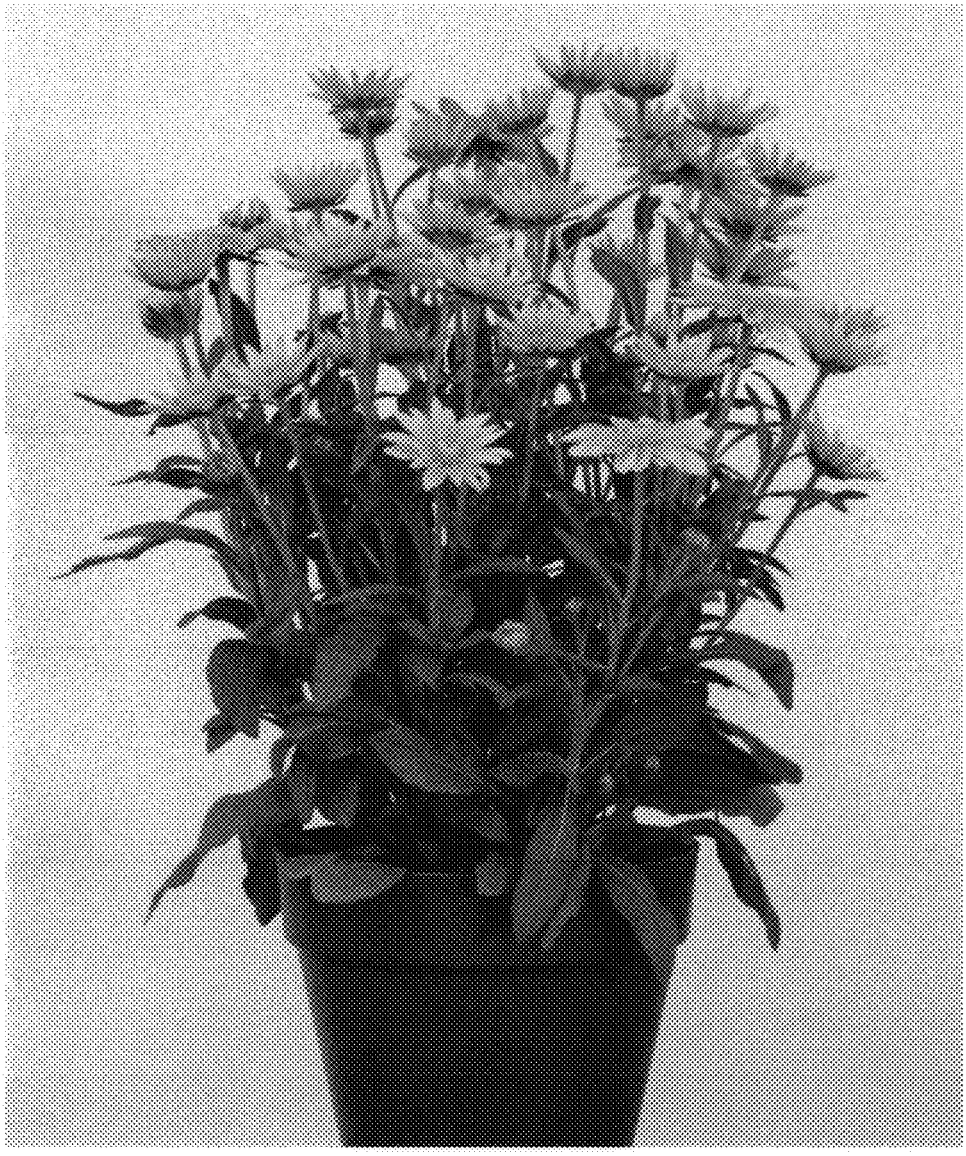
Figure 2:
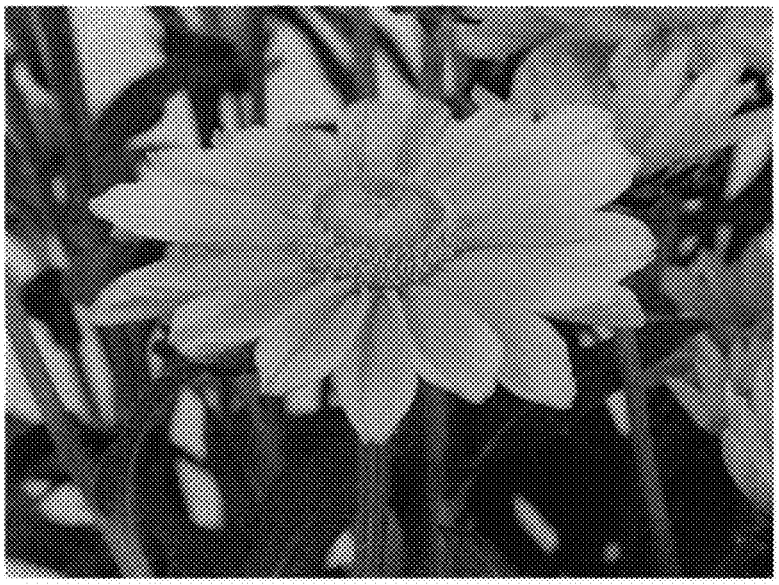

The photograph in FIG. 2 provides a close-up view of an inflorescence of 'RUDLE169'.

Figure 3:
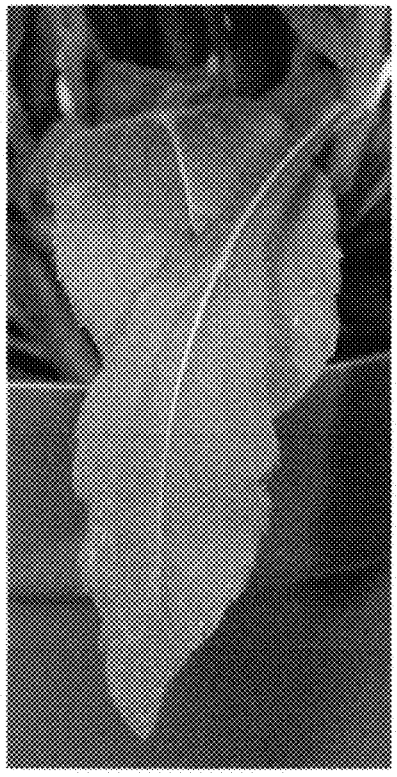

The photograph in FIG. 3 provides a close-up view of the foliage of 'RUDLE169'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDLE169' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 13 weeks from early to late summer in The Netherlands.

*Plant type*.—Herbaceous perennial.

*Plant habit*.—Broadly upright, compact.

*Plant shape*.—Obovate.

*Height and spread*.—Average of 50.8 cm in height from soil level to top of foliar plane and 57.3 cm in height from soil level to top of floral plane, 49.8 cm in diameter.

*Hardiness*.—At least in U.S.D.A. Zones 4 to 10.

*Diseases and pests*.—No susceptibility and resistance to diseases or pests has been observed.

*Root description*.—Fine and fibrous.

*Propagation*.—Tissue culture.

*Root development*.—An average of 3 weeks for root initiation with a young rooted plant produced in an average of 6 weeks.

*Growth rate and vigor*.—Vigorous.

Stem description:

*Shape*.—Moderately angled.

*Stem color*.—Young and mature stems; 144B, 144A at the angles.

*Stem size*.—An average of 4.5 mm in diameter and an average of 20.5 cm in height.

*Stem surface*.—Moderately glossy and densely covered with strigose hairs an average of 2 mm in length and close to NN155D in color.

*Stem number*.—Average of 10 main stems, 8 lateral branches per main stem.

*Internode length*.—An average of 3.4 cm in length.

*Stem aspect*.—Main stems; average of 20° to vertical, lateral branches; average of 20° to main stems.

*Branching*.—Freely branching from base with lateral stems.

Foliage description (cauline leaves):

*Leaf shape*.—Elliptic to ovate and obovate.

*Leaf division*.—Simple.

*Leaf base*.—Cuneate.

*Leaf apex*.—Acute.

*Leaf venation*.—Pinnate, color upper surface 145D, color lower surface 147D.

*Leaf margins*.—Coarsely serrate, coarsely moderately undulate.

*Leaf attachment*.—Petiolate.

*Leaf arrangement*.—Alternate.

*Leaf size*.—Average of 8 cm in length and 3.5 cm in width.

*Leaf color*.—Young upper surface; 138A, young lower surface; 138B, mature upper surface; 137B, mature lower surface; 138A.

*Leaf surface*.—Both surfaces rough to the touch, matte and densely pubescent with short strigose hairs; an average of 2 mm in length and NN155D in color.

*Petioles*.—Average of 3.9 cm in length, flattened, average 1.1 cm in diameter at widest point and 3 mm in width at narrowest point, upper surface color; 145C, margins 137B, lower surface color; 146C, margins 138A, both surfaces slightly glossy and densely covered with strigose hairs; an average of 2 mm in length and N155D in color.

Foliage description (basal leaves): All characteristics match cauline leaves with the following characteristics differing: Arrangement; emerging from base, leaf size: 10 cm in length and 4 cm in width, leaf shape; obovate.

Flower description:

*Type*.—Terminal capitulum, consisting of ray florets and disc florets.

*Capitulum number*.—1 per stem, up to 80 per plant.

*Lastingness of inflorescence*.—Average of 2 weeks, persistent.

*Capitulum size*.—Matures to about 3.2 cm in height and 9.5 cm in diameter, disk size is an average of 1.4 cm in diameter.

*Fragrance*.—None.

*Involucral bracts* (*phyllaries*).—Broadly cuneate base, bluntly acute apex, narrow oblong in shape, entire margins, average of 30 arranged in two rows, 2 cm in length and 4.5 mm in width, color; upper surface when fully open 143A, lower surface when fully open 143B and 144A, both surfaces matt and densely covered with strigose hairs; an average of 1.5 mm in length and NN155D in color.

*Receptacle*.—Dome shaped, an average of 1.4 cm in height and 8 mm in diameter, 157C in color.

*Bracts*.—1 at each disk floret, spirally placed on disc, soft, flattened, an average of 1.25 cm in length and 8 mm in diameter, narrow cuneate in shape, acute apex, narrowly cuneate base, color; apex 145B to 145C with mid-section and base 150D, surface matte and moderately pubescent with hairs; an average of 0.3 mm in length and too small to measure color.

*Buds*.—Globular in shape, immature ray florets pointed upward and curled inward, average of 1.5 cm in length and 2.1 cm in diameter, immature ray florets are 150C in color, immature involucral bracts 138B to 138C in color, surface on involucral bracts and immature ray florets is densely covered with strigose hairs; an average of 1 mm in length and NN155D in color on bracts and 157A in color on ray florets.

*Peduncle*.—Strong, straight on top of main flowering stem, average of 9.5 cm in length and 4.5 mm in diameter, color; 144A and axially striped 143A, surface moderately glossy sand densely covered with short strigose hairs; an average of 2 mm in length and NN155D in color.

*Ray florets*.—Average of 21 (varying between 19 and 24), rotate around the disk, oblong to slightly obovate in shape, average of 4 cm in length and 1.8 cm in width, emarginate to praemorse apex, cuneate base, entire margin, both surfaces are velvety, matte and glabrous, held near horizontal, color; when opening upper surface 7C, lower half 17A, when opening lower surface 2B, when fully open upper and lower surface 9A, lower half 23A, upper surface veins 12A to 13A, changing to 15B at the base, lower surface veins 153D.

*Disk flowers*.—Average about 480 slightly curved and tubular in shape, 12 whorls arranged spirally on a conical receptacle, lower 85% fused into tube, upper 15% free, tubular, about 7 mm in length and 2 mm in width, free lobes have entire margins, apices of free lobes acute, both surfaces glabrous and slightly glossy, color; when opening upper and lower surface 153C, mid-section and base 160D, fully open upper surface 14B, mid-section and base 160D, fully open lower surface 153D, mid-section and base 160D.

Reproductive organs:

*Gynoecium*.—Pistil; 1, 7 mm in length, style; 5.5 mm in length, color; 157D, stigma; cleft, three-parted, decurrent, 2 mm in diameter, 153D in color, ovary; 155A in color.

*Androecium*.—Stamens; 5, filaments; 2 mm in length, 157D in color, anther; narrow oblong in shape, 2.5 mm in length, 0.5 mm in width, 20B in color, pollen; low in quantity and 14B in color.

*Fruit/seed*.—None observed.

It is claimed:

1. A new and distinct cultivar of *Rudbeckia* plant named 'RUDLE169' substantially as herein illustrated and described.

* * * * *